US011122979B2

(12) United States Patent
Heinrich et al.

(10) Patent No.: US 11,122,979 B2
(45) Date of Patent: *Sep. 21, 2021

(54) TRANSCUTANEOUS ORGAN FUNCTION MEASUREMENT

(71) Applicant: MediBeacon Inc., St. Louis, MO (US)

(72) Inventors: Ralf Heinrich, Schwegenheim (DE); Johannes Pill, Leimen (DE); Sabine Neudecker, Ludwigshafen (DE); Daniel Schock-Kusch, Mannheim (DE); Juergen Guenther, Schriesheim (DE); Stefan Koenig, Lorsch (DE); Jochen Friedemann, Altrip (DE)

(73) Assignee: MediBeacon Inc., St. Louis, MO (US)

( * ) Notice: Subject to any disclaimer, the term of this patent is extended or adjusted under 35 U.S.C. 154(b) by 384 days.

This patent is subject to a terminal disclaimer.

(21) Appl. No.: 16/289,529

(22) Filed: Feb. 28, 2019

(65) Prior Publication Data

US 2019/0261862 A1    Aug. 29, 2019

Related U.S. Application Data

(63) Continuation of application No. 15/030,727, filed as application No. PCT/EP2014/072420 on Oct. 20, 2014, now Pat. No. 10,264,977.

(30) Foreign Application Priority Data

Oct. 22, 2013    (EP) .................................... 13189703

(51) Int. Cl.
*A61B 5/00*       (2006.01)
*A61B 5/20*       (2006.01)
*A61B 5/1455*   (2006.01)

(52) U.S. Cl.
CPC .......... *A61B 5/0071* (2013.01); *A61B 5/1455* (2013.01); *A61B 5/201* (2013.01)

(58) Field of Classification Search
CPC ....... A61B 5/0071; A61B 5/201; A61B 5/145; A61B 5/1455; A61B 5/14551; A61B 5/14532

See application file for complete search history.

(56) References Cited

U.S. PATENT DOCUMENTS 4,301,140 A    11/1981   Frank et al.
6,440,389 B1    8/2002   Rabito
(Continued)

FOREIGN PATENT DOCUMENTS

DE         10023051 A1    11/2001
DE    102004048864 A1     4/2006
(Continued)

OTHER PUBLICATIONS

Brenner et al., "Quantitative Importance of Changes in Postglomerular Colloid Osmotic Pressure in Mediating Glomerulotubular Balance in the Rat," The Journal of Clinical Investigation, vol. 52, (1973), pp. 190-197.

(Continued)

*Primary Examiner* — Chu Chuan Liu
(74) *Attorney, Agent, or Firm* — Armstrong Teasdale LLP

(57) ABSTRACT

The present invention relates to a method for determining an organ function in a subject, comprising the steps of: providing a first concentration-time curve obtained by transcutaneously measuring in a body fluid at a first position background fluorescence in at least one first time point and fluorescence of an indicator compound in at least a second, a third, a fourth, a fifth, and a sixth time point; providing a second concentration curve obtained by transcutaneously measuring in a body fluid at a second position background fluorescence in at least one seventh time point and fluorescence of an indicator compound in at least a eighth, a ninth, a tenth, an eleventh, and a twelfth time point; fitting the first and the second concentration curve into a kinetic model (Continued)

representing at least four diffusion compartments; and thereby determining an organ function in a subject. The invention further relates to a device for determining an organ function according to the method of the present invention, said device comprising a first sensor for transcutaneously measuring fluorescence of an indicator at a first position, a second sensor for transcutaneously measuring fluorescence of an indicator at a second position; and a data processing unit for fitting the values obtained by the sensors into a kinetic model of one of the preceding claims. The present invention also relates to a kit comprising a device of the present invention and an indicator compound, as well as to a computer or computer network comprising at least one processor, wherein the computer or computer network is adapted to perform the method according to the present invention.

14 Claims, 5 Drawing Sheets

(56) References Cited

U.S. PATENT DOCUMENTS

| | | | |
|---|---|---|---|
| 2003/0236452 | A1 | 12/2003 | Melker et al. |
| 2004/0022730 | A1 | 2/2004 | Hein et al. |
| 2004/0210280 | A1 | 10/2004 | Liedtke |
| 2006/0020216 | A1 | 1/2006 | Oishi et al. |
| 2006/0095102 | A1 | 5/2006 | Perez |
| 2007/0237678 | A1 | 10/2007 | Roesicke et al. |
| 2008/0281173 | A1 | 11/2008 | Esenaliev et al. |
| 2010/0121170 | A1 | 5/2010 | Rule |
| 2011/0191087 | A1 | 4/2011 | Lehrach et al. |
| 2011/0201940 | A1 | 8/2011 | Wang et al. |
| 2011/0230739 | A1 | 9/2011 | Gretz et al. |
| 2012/0123229 | A1 | 5/2012 | Butterfield et al. |
| 2012/0123247 | A1 | 5/2012 | Hu et al. |
| 2013/0116512 | A1 | 5/2013 | Imran |
| 2013/0116518 | A1 | 5/2013 | Wang et al. |
| 2015/0306486 | A1 | 10/2015 | Logan et al. |

FOREIGN PATENT DOCUMENTS

| | | | |
|---|---|---|---|
| JP | 2008538316 | A | 10/2008 |
| JP | 2011501681 | A | 1/2011 |
| WO | 3931183 | A1 | 6/1999 |
| WO | 200185799 | A1 | 11/2001 |
| WO | 200632441 | A2 | 3/2006 |
| WO | 2010020673 | A2 | 2/2010 |
| WO | 2010093635 | A2 | 8/2010 |

OTHER PUBLICATIONS

Chinen et al., "Fluorescence-Enhanced Europium-Diethylenetriaminepentaacetic (DTPA)-Monoamide Complexes for the Assessment of Renal Function," J. Med Chem., vol. 51, (2008), pp. 957-962.

Dean et al., "Inulin, Diodone, Creatinine and Urea Clearances In Newborn Infants," J. Physiol., vol. 106, (1947), pp. 431-439.

Debreczeny et al., "Transdermal Optical Renal Function Monitoring in Humans: Development, Verification, and Validation of a Prototype Device," Journal of Biomedical Optics, vol. 23, No. 5, (May 2018), pp. 057003-1-057003-9.

Friedman et al., "A comparison of the renal clearances of allantoin and inulin in man," Fed. Proc., vol. 7, No. 1 Pt 1, (1948), 1 page.

Gregory et al., "Studies on Hypertension; Effect of Lowering the Blood Pressures of Hypertensive Patients by High Spinal Anesthesia on the Renal Function as Measured by Inulin and Diodrast Clearances," Arch. Intern. Met (Chic), vol. 77, (1946), pp. 385-392.

Levin et al., "The Effect of Chronic Anemia on Renal Function as Measured by Inulin and Diodrast Clearances," Proc. Annu. Meet. Cent. Soc. Clin. Res. U. S., vol. 20, (1947), 3 pages.

Nagpal et al., "Combined Fluorescein, Indocyanine angiography and Optical Coherent Tomography Using Spectralis," Rajasthan Journal of Ophthalmology, (2011), 8 pages.

Navar et al., "Distal Tubular Feedback in the Autoregulation of Single Nephron Glomerular Filtration Rate," J. Clin. Invest., vol. 53, (1974), pp. 516-525.

Nicholson et al., "Renal Function as Affected by Experimental Unilateral Kidney Lesions : I. Nephrosis Due to Iodium Rartrate," J. Exp. Med., vol. 68, (1938), pp. 439-456.

Pill et al., "Fluorescein-labeled Sinistrin as Marker of Glomerular Filtration Rate," European Journal of Medicinal Chemistry, vol. 40, (2005), pp. 1056-1061.

Poujeol et al., "Glomerular Filtration Rate and Microsphere Distributions in Single Nephron of Rat Kidney," Pflugers Arch., vol. 357, (1975), pp. 291-301.

Robson et al., "The Determination of the Renal Clearance of Inulin in Man," Q. J. Exp. Physiol., vol. 35, (1949), pp. 111-134.

Schock-Kusch et al., "Transcutaneous measurement of glomerular filtration rate using FITC-sinistrin in rats," Nephrol Dial Transplant, vol. 24, (2009), pp. 2997-3001.

Shannon et al., "The Renal Excretion of Inulin and Creatinine by the Anaesthetized Dog and the Pump-Lung-Kidney Preparation", J. Physiol., vol. 98, (1940), pp. 97-108.

Yu et al., "Rapid determination of renal filtration function using an optical ratiometric imaging approach," Am. J. Physiol. Renal. Physiol., vol. 292, (2007), pp. F1873-F1880.

International Search Report received for PCT Patent Application No. PCT/US2019/013784, dated May 7, 2019, 6 pages.

International Preliminary Report on Patentability received for PCT Patent Application No. PCT/US2019/013784, dated Jul. 30, 2020, 8 pages.

International Preliminary Report on Patentability in corresponding International Application No. PC/EP2014/072420, dated Jan. 21, 2016.

Cussler, "Diffusion: Mass Transfer in Fluid Systems", Cambridge University press, Published 1997, Third Edition.

Frennby et al., "Contrast Media as Markers of GFR", 2002, European Radiology, Published May 16, 2001, pp. 475-484, vol. 12, No. 2, Springer International, Berlin, DE.

Mikhail et al., "Rational Approach to Select Small Peptide Molecular Probes Labeled with Fluorescent Cyanine Dyes for in Vivo Optical Imaging", Biochemistry, Published Apr. 5, 2011, pp. 2691-2700, vol. 50, No. 13.

Pais et al., "High-sensitivity, Disposable Lab-on-a-Chip with Thin-Film Organic Electronics for Fluorescence Detection", Lab on a Chip, Published Mar. 20, 2008, pp. 794-800, vol. 8.

Pill et al., "Direct Fluorometric Analysis of a Newly Synthesised Fluorescein-Labelled Marker for Glomerular Filtration Rate", Analytical and Bioanalytical Chemistry, Published May 2005, pp. 59-64, vol. 382, No. 1.

Pill et al., "Fluorescein-Labeled Sinistrin as Marker of Glomerular Filtration Rate", European Journal of Medicinal Chemistry, Published Oct. 2005, pp. 1056-1061, vol. 40, No. 10.

Margouleff, "Blood Volume Determination, A Nuclear Medicine Test in Evolution", Clinical Nuclear Medicine, Published Jul. 2013, pp. 534-537, vol. 38, No. 7.

Probst et al., "Gender Differences in the Blood Volume of Conscious Sprague-Dawley Rats", Journal of the American Association for Laboratory Animal Science, Published Mar. 1, 2006, pp. 49-52, vol. 45, No. 2.

Qi et al., "Serial Determination of Glomerular Filtration Rate in Conscious Mice Using FITC-Inulin Clearance", American Journal of Physiology—Renal Physiology, Published Mar. 1, 2004 pp. F590-F596, vol. 286, No. 3.

Schock-Kusch et al., "Transcutaneous Measurement of Flomerular Filtration Rate Using FITC-Sinistrin in Rats", Nephrology Dialysis Transplantation, Published Oct. 2009, pp. 2997-3001, vol. 24, No. 10.

(56) References Cited

OTHER PUBLICATIONS

Schock-Kusch et al., "Online Feedback-Controlled Renal Constant Infusion Clearances in Rats", Kidney International, Published Aug. 1, 2012, pp. 314-320, vol. 82, No. 3.
Schock-Kusch et al., "Transutaneous Assessment of Renal Function in Conscious Rats with a Device for Measuring FITC-Sinistrin Disappearance Curves", Kidney International, Published Jun. 1, 2011, pp. 1254-1258, vol. 79, No. 11.
Wang et al., "Transgenic Overexpression of GLUTI in Mouse Glomeruli Produces Renal Disease Resembling Diabetic Glomerulosclerosis", American Journal of Physiology—Renal Physiology, Published Jul. 1, 2010, pp. F99-F111, vol. 299, No. 1.
Wang et al., "Rapid Diagnosis and Quantification of Acute Kidney Injury Using Fluorescent Ratio-Metric Determination of Glomerular Filtration Rate in the Rat", American Journal of Physiology—Renal Physiology, Published Nov. 1, 2010, pp. F1048-F1055, vol. 299, No. 5.
Friedemann, "Development of a Pharmokinetic Model to Describe the Distribution and Excretion Kinetics of a Renal Marker Using Transcutaneously Obtained Data in Rats", Dissertation from University Heidelberg, Published 2014, 112 pages.
Pharsight, "WinNonlin User's Guide", Version 5.3, Pharsight Corporation, 710 pages.

TRANSCUTANEOUS ORGAN FUNCTION MEASUREMENT

CROSS-REFERENCE TO RELATED APPLICATIONS

This application is a continuation of U.S. application Ser. No. 15/030,727, filed on Apr. 20, 2016, which is the U.S. national stage entry of PCT/EP2014/072420, filed on Oct. 20, 2014, which claims priority to European Patent Application 13189703.5, filed on Oct. 22, 2013, all of which are incorporated by reference in their entirety.

The present invention relates to a method for determining an organ function in a subject, comprising the steps of: providing a first concentration-time curve obtained by transcutaneously measuring in a body fluid at a first position background fluorescence in at least one first time point and fluorescence of an indicator compound in at least a second, a third, a fourth, a fifth, and a sixth time point; providing a second concentration curve obtained by transcutaneously measuring in a body fluid at a second position background fluorescence in at least one seventh time point and fluorescence of an indicator compound in at least a eighth, a ninth, a tenth, an eleventh, and a twelfth time point; fitting the first and the second concentration curve into a kinetic model representing at least four diffusion compartments; and thereby determining an organ function in a subject. The invention further relates to a device for determining an organ function according to the method of the present invention, said device comprising a first sensor for transcutaneously measuring fluorescence of an indicator at a first position, a second sensor for transcutaneously measuring fluorescence of an indicator at a second position; and a data processing unit for fitting the values obtained by the sensors into a kinetic model of one of the preceding claims. The present invention also relates to a kit comprising a device of the present invention and an indicator compound, as well as to a computer or computer network comprising at least one processor, wherein the computer or computer network is adapted to perform the method according to the present invention.

In the clinical and preclinical field, determining various organ functions is accorded great importance since, for example, corresponding therapies or medications can be controlled in accordance with said organ functions. The invention is described hereinafter substantially with regard to the kidney function. In principle, however, other applications are also conceivable in which the function of a particular organ can be detected by means of the means and methods described herein. Thus, in principle, it is possible to use any desired exogenous or endogenous substances in the blood as indicator substances.

In kidney diagnostics, the quantitative and qualitative functional testing of the kidneys is of great significance. One indicator of the kidney function is the so-called glomerular filtration rate (GFR) which indicates the amount of primary urine produced by the glomeruli of the kidneys per unit time.

For quantifying the GFR, several methods are known from the prior art and medical practice. One class of methods, into which the present invention may also be classified, is based on the use of one or a plurality of indicator substances, which are at least predominantly removed from the blood on account of the kidney function. This means that the indicator substance is removed from the body at least predominantly by the filtration effect of the glomeruli, in which case substantially neither tubular secretion nor resorption from the primary urine takes place. Clearance is generally designated as that amount of plasma in milliliters which is freed of the indicator substance per minute.

Various exogenous and/or endogenous indicator substances are known for determining the glomerular filtration rate. Examples of endogenous indicator substances are creatinine or cystatin C. Various exogenous indicator substances are also known from the prior art. More particularly, saccharides, e.g. polyfructosans, can be used as indicator substances. Examples of suitable indicator substances are disclosed in WO2001/85799 or WO2006/32441. It is generally possible to have recourse to this prior art in the context of the present invention as well.

From a metrological standpoint, one of the challenges consists, in particular, in determining the concentration profile of the indicator substance and thus the clearance thereof. Numerous different methods by means of which the clearance can be detected metrologically are compiled in WO 99/31183. Thus, some of the methods are based on the fact that blood and/or urine samples are taken at regular or irregular intervals, and the concentration of the marker substance is determined analytically, for example by means of enzymatic detection methods. Other methods are based on the use of radioactive indicator substances and/or X-ray contrast media. The acceptance of such indicator substances by the patient is generally low, however. Methods based on determining the renal clearance by means of chemical or biochemical analysis or on the use of radioactive indicator substances are generally complex and burdened with high errors. In routine clinical practice, therefore, in many cases the kidney function is estimated on the basis of approximation formulae, which, however, are likewise very inaccurate and can have error tolerances in the range of 30 to 40%.

The prior art therefore likewise discloses methods based on the use of fluorescent markers. In this case, use is made of indicator substances marked with dyes that can be detected optically. By way of example, these can be fluorescent markers which are admixed with the indicator substances or bonded to the indicator substances, for example by covalent bonding. Examples of marked indicator substances are described in WO2001/85799 or WO2006/32441, in which case it is possible to have recourse to these marked indicator substances, for example, in the context of the present invention.

In the latter methods mentioned, therefore, an optical signal is used as a measure of the concentration of the indicator substance. In this case, the respective concentration of the indicator substance can be deduced for example from a known relation between the optical signal and the concentration. Said known relation can be, for example, of an empirical, semi-empirical or analytical nature, for example a relation determined by means of calibration measurements. Thus, in DE 100 23 051 A1, for example, the indicator substance used is sinistrin marked with fluoresceinisothiocyanate (FITC). In this case, a noninvasive, transcutaneous measurement of the FITC fluorescence signal by means of a noninvasive measuring head is described, inter alia. Said measuring head is configured as a fiber-optic measuring head in which an external light source, via an optical fiber, illuminates the skin and excites the FITC-sinistrin molecules contained therein. The fluorescent light emitted by the FITC is in turn picked up by means of optical fibers and forwarded to an external detector.

However, the measurement of the fluorescence signals as described in DE 100 23 051 A1 is extremely complex in terms of apparatus technology. This is because it is necessary to provide complex spectrographs in order to evaluate the measurement signals. Moreover, a fiber-optic system is required which, on account of the associated losses of excitation light, necessitates the use of highly intensive light sources, more particularly lasers. The fiber-optic system, together with the complex light sources and lasers, has the effect, however, that a measurement of the renal clearance cannot be carried out in an ambulant manner or by means of portable equipment, but rather practically exclusively in optical laboratories specifically designed for this purpose.

Similar indicator substances as described above have also been disclosed in WO2010/020673. However, in this document a simplified method of measurement is described, using a portable sensor e.g. in the form of a plaster.

Numerous further analysis systems which, in principle, are also suitable for portable equipment are generally known from other fields of medical diagnostics. Thus, US 2004/0210280 A1, for example, describes a plaster-like system which can be used for transdermal therapy and diagnosis. Said document proposes, inter alia, that the system independently collects and takes up fluid samples from the skin. In A. Pais et al: High-sensitivity, disposable lab-on-a-chip with thin-film organic electronics for fluorescence detection, Lab Chip, 2008, 8, 794-800, a disposable lab-on-a-chip test element is proposed. The latter is based on an organic light-emitting diode and an organic photodetector. The test element is configured as a microfluidic test element and is able to analyze liquid samples by means of fluorescence detection. DE 10 2004 048 864 A1 describes an analytical test element with wireless data transmission which is used for determining the concentration of an analyte from a body fluid. Said document proposes configuring at least a portion of the electrical components of the system on the basis of polymer electronics. US 2006/020216 A1 describes a portable health management apparatus that can be used, in particular, for a blood pressure measurement. Said document proposes, inter alia, measuring the movement of the blood within a blood vessel by means of light absorption of light incident transdermally.

Generally, for kidney function testing in the prior art, recourse is regularly made to inulin as the gold standard. In this case, the inulin measurement is usually effected enzymatically in a serum or urine sample. Noninvasive methods using fluorescence-marked inulin yielded ambiguous results (WO2001/85799). FITC sinistrin was established as the standard for fluorescence-based GFR determinations (WO2001/85799; Pill 2005, Anal Bioanal Chem 382: 59-64; Pill 2005, Europ J Medicinal Chem 40: 1056-1061), wherein here as well the measurements were predominantly effected in isolated samples.

However, these last-mentioned methods and devices known from the prior art either require sampling of blood and/or urine samples, which decreases acceptance by the patient, or they do not allow to directly determine the GFR or a parameter proportional thereto. For this reason, many methods determine plasma clearance of an indicator compound as an approximation (reviewed in Frennby et al. (2002), Eur. Radiol 12: 475).

Consequently, one object of the present invention is to provide devices and methods for determining organ functions, more particularly a kidney function, which avoid the disadvantages of known devices and methods. More particularly, the intention is to provide a method of determining the GFR of a subject. This object is achieved by means of the invention with the features of the independent claims. Advantageous developments of the invention, which can be realized individually or in combination, are presented in the dependent claims.

DETAILED DESCRIPTION

Figure 1A:
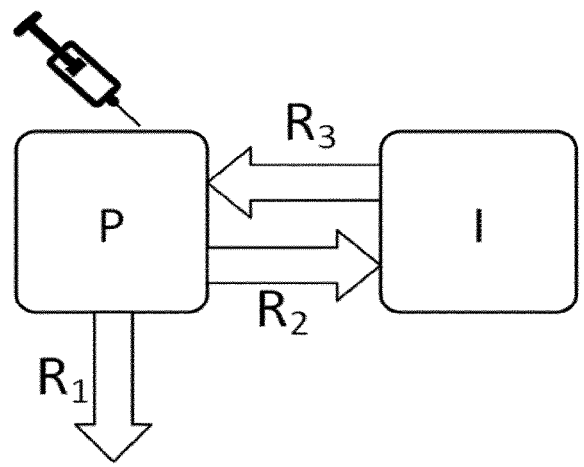
FIG. 1A shows a graphical representation of a 2-compartment model for renal function measurement.

Accordingly, the present invention relates to a method for determining an organ function in a subject, comprising the steps of:

a) providing a first concentration-time curve obtained by transcutaneously measuring in a body fluid at a first position (i) background fluorescence in at least one first time point and (ii) fluorescence of an indicator compound in at least a second, a third, a fourth, a fifth, and a sixth time point, b) providing a second concentration-time curve obtained by transcutaneously measuring in a body fluid at a second position (i) background fluorescence in at least one seventh time point and (ii) fluorescence of an indicator compound in at least a eighth, a ninth, a tenth, an eleventh, and a twelfth time point, c) fitting the first and the second concentration-time curve into a kinetic model representing at least four diffusion compartments, and d) thereby determining an organ function in a subject.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which a solely and exclusively consists of B) and to a situation in which, besides B, one or more further elements are present in entity A, such as element C, elements C and D or even further elements. From this, it is understood by the skilled person that the method of the present invention may, e.g., comprise obtaining more than two concentration-time curves.

Further, as used in the following, the terms "preferably", "more preferably", "most preferably", "particularly", "more particularly", "specifically", "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such way with other optional or non-optional features of the invention.

As used herein, the term "subject" relates to an animal, preferably a mammal, more preferably a farm or companion animal. Most preferably, the subject is a human.

The term "organ function", as used herein, relates to the activity of an organ of a subject of mediating and/or controlling passage of compounds to or from blood. Thus, preferably, the term relates to brain-blood barrier function, intestinal wall barrier function, lung function, liver function, or pancreas function. More preferably, the term relates to kidney function. It is understood by the skilled person that the term "determining organ function", as used herein, preferably relates to determining a measurable parameter indicating, preferably being proportional, to the function of the respective organ. It is also understood by the skilled person that an organ may have more than one function and that distinct parameters may be measured in order to determine distinct functions of an organ. Thus, preferably, determining renal function relates to determining the GFR.

As used herein, the term "providing a concentration-time curve" relates to making available a concentration-time curve as detailed herein below. Preferably, providing a concentration-time curve relates to obtaining a measuring curve according to the present invention. Thus, more preferably, providing a first concentration-time curve is obtaining a first concentration-time curve by transcutaneously measuring in a body fluid at a first position (i) background fluorescence in at least one first time point and (ii) fluorescence of an indicator compound in at least a second, a third, a fourth, a fifth, and a sixth time point, and wherein providing a second concentration-time curve in step b) is obtaining a second concentration-time curve by transcutaneously measuring in a body fluid at a second position (i) background fluorescence in at least one seventh time point and (ii) fluorescence of an indicator compound in at least a eighth, a ninth, a tenth, an eleventh, and a twelfth time point. As indicated above, for both concentration-time curves fluorescence is measured in at least one time point before administering the indicator substance to measure the background signal (baseline). It is understood by the skilled person that the term may include further steps, e.g., preferably, contacting a subject to a measuring device, recording measurement values, and the like.

The term "indicator compound", as used herein, relates to a compound emitting photons at an emission wavelength upon or after irradiation with photons at at least one excitation wavelength. It is understood by the skilled person that, preferably, the emission wavelength is non-identical to the excitation wavelength. More preferably, the emission wavelength is shorter than the excitation wavelength ("up-conversion"). Most preferably, the emission wavelength is longer than the excitation wavelength. In principle, compounds providing for all kinds of luminescence are suitable for the method of the present invention. However, compounds emitting light within a short time after irradiation are preferred; thus, preferably the indicator compound re-emits absorbed radiation on average within less than one s, more preferably within less than one ms, even more preferably within less than a µs. Thus, most preferably, the indicator compound of the present invention is a fluorescent compound.

Preferably, the indicator compound of the present invention is an endogenous compound, i.e. a compound present in and/or produced in the body of the subject. More preferably, the indicator compound is an exogenous compound, i.e. a compound not normally found in the body of said subject. It is understood by the skilled person that an endogenous compound may be administered to a subject in order to increase its concentration in the blood.

Preferably, the indicator compound comprises a fluorescent low-molecular weight compound covalently bound to a hydrophilic compound. Preferably, the indicator compound has a molar mass of less than 20 kg/mol, more preferably less than 10 kg/mol, even more preferably less than 5 kg/mol, and most preferably less than 3 kg/mol. Preferably, the indicator compound is a zwitterionic or an acidic compound; more preferably, the indicator compound is a neutral compound, most preferably, the indicator compound is a basic compound. Preferably, the hydrophilic compound is selected from the list consisting of oligo- and polysaccharides, oligo- and polyalcohols, and oligo- and polyethers. Preferably, the oligosaccharide is a cyclodextrin, a fructan, or a dextran. Also preferably, the oligoalcohol is oligovinylalcohol and the polyalcohol is polyvinylalcohol. Also preferably, the polyether is polyethylenglycol (PEG). Preferably, the indicator compound is a pharmacologically acceptable compound or can be provided in a pharmacologically acceptable preparation.

The indicator compound is applied to the subject by any method suitable to ensure distribution in the blood of the subject. Thus, preferably, orally available indicator compounds may be used. More preferably, the indicator compound is administered to the blood stream of the subject, preferably intraarterially or intravenously. Preferably, the indicator compound is administered as a continuous infusion. More preferably, the indicator compound is administered as a bolus injection.

As used herein, the term "measuring fluorescence" relates to determining fluorescence of the indicator compound comprised in a subject semiquantitatively or, preferably, quantitatively. Methods of measuring fluorescence are well-known in the art and generally include irradiating an indicator compound with photons having an excitation wavelength and detecting photons emitted by the indicator compound as a result of excitation irradiation. Suitable means for irradiating and detecting are described herein below. Preferably, measuring fluorescence is achieved by one of the sensory devices described in WO2010/020673.

Preferably, fluorescence at a first position is measured at at least six non-identical points in time, i.e. at a first, a second, a third, a fourth, a fifth, and a sixth point in time, wherein at the first point in time, background fluorescence is determined. Thus, a first data set is provided consisting of at least six data pairs of a point in time, each correlated with a value of fluorescence of the indicator compound. It is understood by the skilled person that said first data set corresponds to the change of concentration of the indicator compound in the body fluids relevant for measurement at said first position. Thus, this data set can be used to establish a concentration-time curve corresponding to the concentration change of the indicator compound in the tissue under said first position. Preferably, the value measured as background fluorescence at the first point in time is subtracted from the values measured at the second to sixth points in time to provide corrected measurement values.

Also preferably, fluorescence at a second position is measured at at least six non-identical points in time, i.e. at a seventh, an eighth, a ninth, a tenth, an eleventh, and a twelfth point in time. Thus, a second data set is provided consisting of at least six data pairs of a point in time, each correlated with a value of fluorescence of the indicator compound. It is understood by the skilled person that said second data set corresponds to the change of concentration of the indicator compound in the body fluids relevant for measurement at said second position. Thus, this second data set can be used to establish a concentration-time curve corresponding to the concentration change of the indicator compound in the tissue under said second position. Preferably, the value measured as background fluorescence at the seventh point in time is subtracted from the values measured at the second to sixth points in time to provide corrected measurement values.

Preferably, the time frame encompassed by the first to sixth points in time overlaps with the time frame encompassed by the seventh to twelfth point in time. More preferably, said time frames overlap by at least 50% of the duration of the shorter time frame. Most preferably, said time frames are the same. Preferably, the first to sixth and the seventh to twelfth point in time are evenly spaced over the respective time frame encompassed. Preferably, measuring at the at least two positions is performed alternatingly, i.e., a measurement at a first position is followed by a measurement at a second position and vice versa. More preferably, measuring fluorescence of an indicator compound at a first and a second position is done simultaneously, i.e. measuring at the first and the seventh point in time is performed at the same point in time, i.e. simultaneously, measuring at the second and the eighth point in time is performed at the same point in time, and the like.

Preferably, the points in time of measuring are selected such that the first and seventh point in time lie before application of the indicator compound, such that at least one of the second to fifth and of the eighth to eleventh points in time lies such that the concentration of the indicator compound in blood is increasing with time, and such that at least one of the third to sixth and of the ninth to twelfth points in time lies such that the concentration of the indicator compound in blood is decreasing with time. As will be appreciated by the skilled person, such selection of time point is preferably achieved by obtaining measurement values at regular intervals and by selecting the relevant points in time as described above afterwards. Preferably, the selection of time points as described above is assisted by an appropriate algorithm. It is understood by the skilled person that the concentration of the indicator compound may be unchanged or essentially unchanged between two adjacent points in time, e.g. in case the GFR is measured and the subject is afflicted with renal failure. Thus, most preferably, the points in time are selected such that the concentration of the indicator compound is first increasing then decreasing with time in a healthy reference subject.

Thus, in case the organ function is renal function or the GFR, preferably, the first and seventh point in time of measurement are selected 0 to 1 hour before administration of the indicator compound and the later points in time of measurement are selected in the range of 0 to 24 hours after administration of the indicator compound. More preferably, the first and seventh point in time of measurement are selected 0 to 0.5 hour before administration of the indicator compound and the later points in time of measurement are selected in the range of 0 to 12 hours after administration of the indicator compound. Most preferably, the first and seventh point in time of measurement is selected 0 to 0.25 hour before administration of the indicator compound and the later points in time of measurement are elected in the range of 0 to 6 hours after administration of the indicator compound. Preferably, in such a case all points in time of measuring are within 8 hours, more preferably within 6 hours, even more preferably within 4 hours, or, most preferably, within 2 hours. It is, however, understood by the skilled person, that especially in the case of impaired organ function, longer measurement intervals may be required and that in such case the measurement period may extend beyond 8 hours. Thus, in a preferred embodiment, the method of the present invention comprises a step of first determining the concentration of the indicator compound at two non-identical points in time, and, based on the result of said measurements, deciding on the interval of measurement.

The term "concentration-time curve" is understood by the skilled person and, preferably, relates to a mathematical correlation of the change in concentration of an indicator compound in a body fluid of a subject with time. Thus, the concentration-time curve may comprise a plurality of concentration values acquired at different points in time. The concentration values may be acquired at a constant rate and/or at predetermined or known points in time. Specifically in case a constant acquisition rate is used, the measurement curve may simply contain a sequence of concentration values. The measurement curve, additionally, may comprise time information for each concentration values. Thus, as an example, the measurement curve may contain value pairs, each value pair comprising a concentration value and time information regarding acquisition time of the respective concentration value. Accordingly, a concentration-time curve is, preferably, obtained by determining at least six concentration values at non-identical points in time and correlating the time/concentration pairs thus obtained mathematically, e.g. in a concentration over time graph or in a database. Since in dilute solutions the fluorescence of an indicator compound is proportional to the concentration of said indicator compound, the skilled person understands that a concentration-time curve may also be represented by a mathematical correlation of the change in fluorescence of an indicator compound in a body fluid of a subject with time.

The terms "transcutaneous" and "transcutaneously", as used herein, relate to a mode of measurement wherein at least one of providing photons for illuminating the indicator compound present in the blood, preferably the interstitial fluid of a subject, and detecting light emitted by said indicator compound is performed on the body surface of a subject. Preferably, both providing photons for illuminating the indicator compound and detecting light emitted by the indicator compound are performed on the body surface of a subject. The term "body surface" relates to all outer or inner surfaces of a body connected to the surrounding environment. Thus, preferably, the body surface of the present invention is a part of the body accessible without performing a surgical measure like, e.g. incision, or cutting the skin. Preferably, the body surface is mucosa or a skin, more preferably a non- or moderately hirsute section of the skin. Preferably, the body surface is the skin of a finger or toe, of an arm or leg, or of the torso, or a fingernail or a toenail.

The terms "interstitial fluid" and "interstitium", as used herein, relate to the intrabodily liquid surrounding cells of a subject outside of blood vessels. As appreciated by the skilled person, the term preferably excludes fluid within epithelial lined body cavities, like, e.g. cerebrospinal fluid, joint fluid, and bladder urine.

The term "position", as relating to measurement at a specific position, relates to a point on the body surface of a subject. Preferably, the position is selected as to enable reliable and, more preferably, unobstructive measurement. According to the present specification, the first position and the second position are non-identical, meaning that at least one of the light path between light source and indicator compound molecules and the light path between indicator compound molecules and the detector are non-identical for said two positions. More preferably, both the light path between light source and indicator compound molecules and the light path between indicator compound molecules and the detector are non-identical for said two positions. In a preferred embodiment, the first position is different from the second position, meaning that the first position is separated by at least 0.001 m from the second position; more preferably the first position is separated by at least 0.005 m from the second position, even more preferably by at least 0.01 m, most preferably by at least 0.1 m.

The term "kinetic model", as used herein, relates to a kinetic model of concentration change of a compound in a diffusion compartment. Such models are, in principle, known from the prior art and are discussed in detail in the Examples of the present invention.

The same mathematical basis can be applied to models describing two- or more compartment models. Preferably, the kinetic model of the present invention is a three-compartment model. Preferably, in case the organ function is renal function, the four-compartment model is based on the following assumptions: (i) the four compartments relevant for distribution of the indicator compound are plasma, interstitial fluid, the local interstitium at the position of measurement, and a distribution compartment, corresponding to the container containing the indicator compound before application to the body of the subject; (ii) the indicator compound is eliminated only from plasma, not from the other compartments; (iii) the indicator compound is distributed from the distribution compartment into plasma (iv) the indicator compound is distributed between plasma and interstitial fluid in both directions; (v) the concentration of the indicator compound in the distribution compartment at time 0 is maximal; (vi) the time required for distribution of the indicator compound from the distribution compartment is >0, meaning that the plasma concentration of the indicator compound at the time of application is not the maximal concentration obtainable; (vii) the local interstitium exchanges indicator compound with the plasma compartment, and (viii) exchange with the small volume of the local interstitium does not change the concentration of the indicator compound in plasma, or the interstitial fluid, respectively.

Preferably, in case the organ function is renal function, the concentration-time curves obtained are fitted into said four compartment model. Preferably, a result of said fitting is the GFR per plasma volume of the subject. More preferably, the GFR is calculated from the aforementioned result by multiplication of said result with the plasma volume of the subject. It is understood by the skilled person that the aforementioned calculation of the GFR from the result of the curve fit may also be included as a further calculation step after fitting the concentration-time curves, such that the GFR is issued directly as the result. Preferably, fitting is performed by processing the data underlying the concentration-time curves with a data processing unit, e.g., preferably, a computer or computer network.

It is understood by the skilled person that, based on the above assumptions, a kinetic model can be established and that the concentration-time curves obtained by measuring the concentration at a first and a second position at at least six points in time, respectively, can be fitted into the aforementioned kinetic model, as disclosed herein in the Examples. Preferably, fitting is performed by estimating the optimal values of the relevant parameters, e.g. GFR/VP, the exponentials lambda 1 . . . lambda3, R3,L/VI,L using a suitable mathematical method, e.g. Reduced Chi-Square. Preferably, fitting is performed by processing the data underlying the concentration-time curves with a data processing unit, e.g., preferably, a computer or computer network.

Preferably, the plasma volume of a subject is determined by one of the methods known to the skilled person as explained e.g. in Margouleff (2013) Clin Nucl Med. 38(7): 534-7 or in Wang et al. (2010) Am J Physiol Renal Physiol. 299(5): F1048-55. More preferably, the plasma volume of the subject is determined from the body mass of the subject according to empirical data available e.g. from Probst et al. (2006), Journal of the American Association for Laboratory Animal Science: JAALAS, 45(2): 49.

In another preferred embodiment, fitting the first and the second concentration-time curve into a kinetic model representing at least four diffusion compartments comprises fitting said first and second concentration-time curve into a three-compartment model followed by incorporating a fourth compartment into the results of said fitting.

Preferably, the method of the present invention is modified or complemented by one or more of the following further steps:

Preferably, before obtaining a concentration-time curve, fluorescence of an indicator compound in a body fluid is measured at least two points in time and it is determined whether said two fluorescence values differ significantly, and the intervals between the first to fifth and the sixth to tenth points in time are adjusted depending on the result of said determination.

Also preferably, data sets for concentration-time curves are obtained continuously and a quality control algorithm is applied to the fitting of the concentration-time curves, and a signal is provided when the data permit determination of an organ function within a predefined significance range. It is understood by the skilled person that said signal may e.g., preferably, be termination of measuring fluorescence.

Advantageously, it was found in the work underlying the present invention that an organ function, preferably renal function, more preferably the GFR, can be determined by measuring the change of concentration of an indicator compound in a subject transcutaneously. In particular, it was found that by applying suitable mathematical models and by recording two concentration-time curves at two distinct positions on the skin of a subject, local parameters can be eliminated from the calculations, such that as a direct result of curve fitting the GFR per plasma volume of the patient is obtained. Since the method of the present invention is also applicable in cases where the marker is applied in a bolus injection, the GFR can be determined without any further incision of the body surface of the subject. Where suitable orally applicable markers are used, the whole determination can be accomplished non-invasively.

The definitions made above apply mutatis mutandis to the following. Additional definitions and explanations made further below also apply for all embodiments described in this specification mutatis mutandis.

The present invention also relates to a device for determining an organ function according to the method of the present invention, said device comprising a) a first sensor for transcutaneously measuring fluorescence of an indicator at a first position, b) a second sensor for transcutaneously measuring fluorescence of an indicator at a second position; and c) a data processing unit for fitting the values obtained by the sensors into a kinetic model according to the present invention.

The term "device", as used herein, relates to a system of means comprising at least the aforementioned means operatively linked to each other as to allow the determination. Preferred means for transcutaneously measuring fluorescence of an indicator compound, and means for carrying out the fitting are disclosed herein above in connection with the method of the invention and below in connection with disclosure related to data processing. How to link the means in an operating manner will depend on the type of means included into the device. For example, where means for transcutaneously measuring fluorescence of an indicator compound are applied, the data obtained by said transcutaneously measuring fluorescence of an indicator compound can be processed by, e.g., a computer program in order to obtain the desired results. Preferably, the means are comprised by a single device in such a case. Said device may accordingly include two sensor units for transcutaneously measuring fluorescence of an indicator compound and a computer unit for processing the resulting data for the evaluation.

As used herein, the term "sensor" relates to a device or part thereof enabling the detection of photons emitted by an indicator compound upon irradiation with an excitation light. Preferably, the sensor unit additionally comprises a source of excitation light. The person skilled in the art will realize how to link the means without further ado. Preferred sensors are disclosed e.g. in WO2010/020673, e.g. a sensor in the form of a sensor plaster. Preferably, two sensors, e.g. sensor plasters, are operatively linked in that the data processing unit of the system brings together the results of the measurements performed by the sensors and fits the data into the kinetic model. The sensors may appear as separate devices in such an embodiment and are, preferably, packaged together as a kit. It is, however, also envisaged that two sensor units may be comprised in one casing, preferably in cases where the distance between the first and the second measurement position is short. In another preferred embodiment, one source of excitation light is arranged in such a way that the indicator compound at two different measurement positions is irradiated. Preferred devices are those which can be applied without the particular knowledge of a specialized clinician. The results may be given as output of raw data which need interpretation by the clinician. Preferably, the output of the device is, however, processed, i.e. evaluated, raw data the interpretation of which does not require a clinician.

Preferably, the device further comprises a data storage unit comprising at least reference values of total plasma volume correlated to body mass. As described herein above, in case the organ function is the GFR and in case the body mass of the subject is provided, the device may directly calculate the GFR from the result of fitting the concentration-time curves to the kinetic model in combination with the plasma volume estimate derived from the body mass of said subject.

Moreover, the present invention relates to a kit comprising a device of the present invention and an indicator compound.

The term "kit", as used herein, refers to a collection of the aforementioned compounds, means or reagents of the present invention which may or may not be packaged together. The components of the kit may be comprised by separate units (i.e. as a kit of separate parts). Moreover, it is to be understood that the kit of the present invention is to be used for practicing the method referred to herein above. It is, preferably, envisaged that all components are provided in a ready-to-use manner for practicing the method referred to above. Further, the kit preferably contains instructions for carrying out said method. The instructions can be provided by a user's manual in paper or electronic form. Preferably, the manual comprises instructions for interpreting the results obtained when carrying out the aforementioned method using the kit of the present invention. Alternatively or in addition, the manual preferably comprises reference values of plasma volume in dependence of the body mass of a subject.

Also, the present invention relates to a computer program, wherein the computer program is adapted to perform the method according to one of the preceding claims relating to a method while the program is being executed on a computer.

Thus, the invention further discloses and proposes a computer program including computer-executable instructions for performing the method according to the present invention in one or more of the embodiments enclosed herein when the program is executed on a computer or computer network. Specifically, the computer program may be stored on a computer-readable data carrier. Thus, specifically, one, more than one or even all of method steps a) to d) as indicated above may be performed or assisted by using a computer or a computer network, preferably by using a computer program. Specifically, method steps c) and d) may fully or partially be performed by using a computer or computer network. Method steps a) and/or b) may fully or partially be embodied by using a computer or a computer network, such as by providing the first and second concentration-time curves by the computer or computer network. Thus, generally, "obtaining" the first and second measurement curves may also imply providing the measurement curves, such as by providing the measurement curves as stored in a data memory or data base, for processing in steps c) and d).

The invention further discloses and proposes a computer program product having program code means, in order to perform the method according to the present invention in one or more of the embodiments enclosed herein when the program is executed on a computer or computer network. Specifically, the program code means may be stored on a computer-readable data carrier.

Further, the invention discloses and proposes a data carrier having a data structure stored thereon, which, after loading into a computer or computer network, such as into a working memory or main memory of the computer or computer network, may execute the method according to one or more of the embodiments disclosed herein.

The invention further proposes and discloses a computer program product with program code means stored on a machine-readable carrier, in order to perform the method according to one or more of the embodiments disclosed herein, when the program is executed on a computer or computer network. As used herein, a computer program product refers to the program as a tradable product. The product may generally exist in an arbitrary format, such as in a paper format, or on a computer-readable data carrier. Specifically, the computer program product may be distributed over a data network.

Finally, the invention proposes and discloses a modulated data signal which contains instructions readable by a computer system or computer network, for performing the method according to one or more of the embodiments disclosed herein.

Preferably, referring to the computer-implemented aspects of the invention, one or more of the method steps or even all of the method steps of the method according to one or more of the embodiments disclosed herein may be performed or assisted by using a computer or computer network. Thus, generally, any of the method steps including provision and/or manipulation of data may be performed by using a computer or computer network. Generally, these method steps may include any of the method steps, typically except for method steps requiring manual work, e.g. certain aspects of performing the actual measurements.

Specifically, the present invention further discloses:

A computer or computer network comprising at least one processor, wherein the processor is adapted to perform the method according to one of the embodiments described in this description, a computer loadable data structure that is adapted to perform the method according to one of the embodiments described in this description while the data structure is being executed on a computer, a computer program, wherein the computer program is adapted to perform the method according to one of the embodiments described in this description while the program is being executed on a computer, a computer program comprising program means for performing the method according to one of the embodiments described in this description while the computer program is being executed on a computer or on a computer network, a computer program comprising program means according to the preceding embodiment, wherein the program means are stored on a storage medium readable to a computer, a storage medium, wherein a data structure is stored on the storage medium and wherein the data structure is adapted to perform the method according to one of the embodiments described in this description after having been loaded into a main and/or working storage of a computer or of a computer network, and a computer program product having program code means, wherein the program code means can be stored or are stored on a storage medium, for performing the method according to one of the embodiments described in this description, if the program code means are executed on a computer or on a computer network.

All references cited in this specification are herewith incorporated by reference with respect to their entire disclosure content and the disclosure content specifically mentioned in this specification.

Figure Legends

Figure 1B:
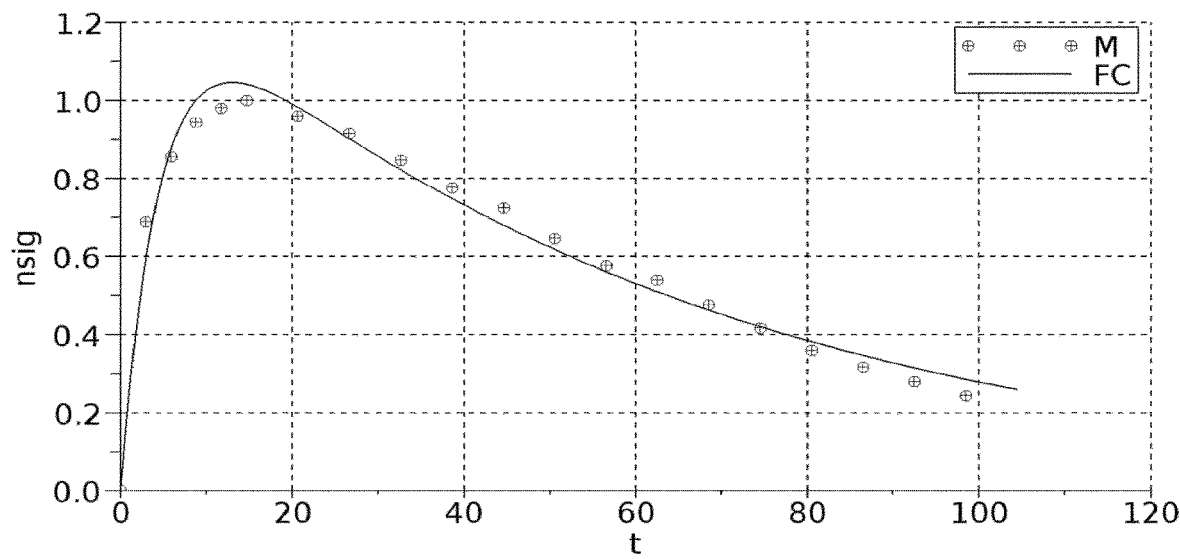
FIG. 1B shows a fitting of an example measurement with the resulting 2-compartment-model equation.

FIG. 1:
A: A graphical representation of the 2-compartment model for renal function measurement.
B: Fitting of an example measurement with the resulting 2-compartment-model equation.
FIG. 2:
A: A graphical representation of the 3-compartment model for renal function measurement.
B: Fitting of an example measurement with the resulting 3-compartment-model equation.
FIG. 3:
A: A graphical representation of the 4-compartment model for renal function measurement.
B: Example measurement with four simultaneously recorded concentration-time curves.
C: Measurement of bolus injection followed by constant infusion until steady state is reached.

Figure 4:
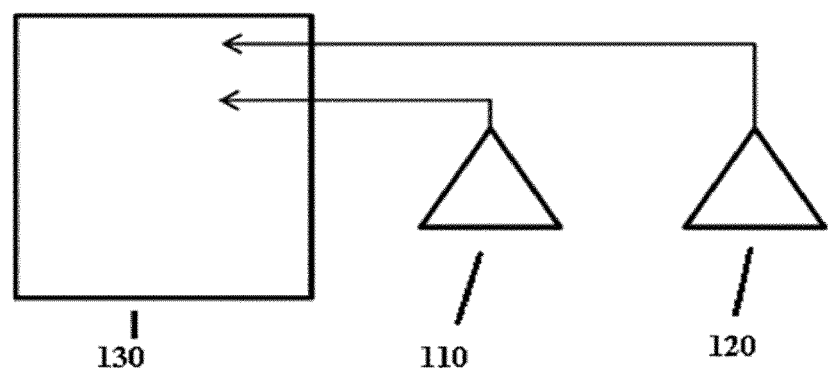
FIG. 4 shows an exemplary device according to the present invention, comprising a first sensor, a second sensor and a data processing unit.

FIG. 4: An exemplary device according to the present invention, comprising a first sensor 110, a second sensor 120 and a data processing unit 130.

LIST OF REFERENCE SYMBOLS t time in minutes
nsig normalized signal
D device
H distribution compartment
P plasma compartment
I interstitial compartment
I,L local interstitial compartment
R diffusion rate x interfacial area
M measured data points
FC fitted curve
110 first sensor
120 second sensor
130 data processing unit The following Examples shall merely illustrate the invention. They shall not be construed, whatsoever, to limit the scope of the invention.

EXAMPLE 1

Two-Compartment Model

A graphical representation of the two-compartment model for renal function measurement known in the art is shown in FIG. 1A.

Example 2

Three-Compartment Model

Figure 2A:
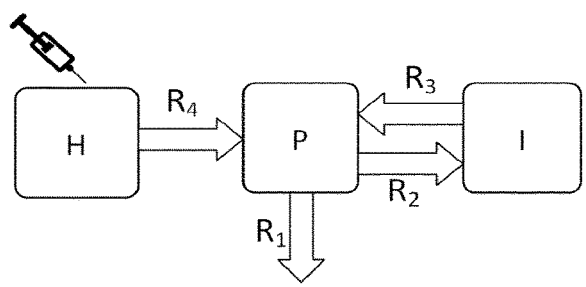
FIG. 2A shows a graphical representation of a 3-compartment model for renal function measurement.
Figure 2B:
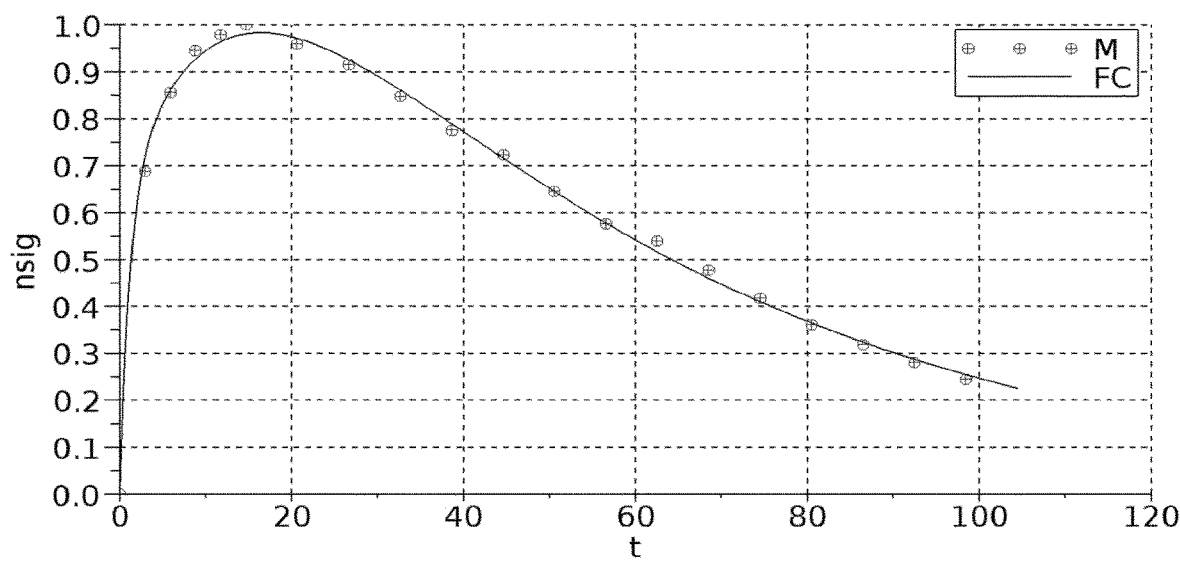
FIG. 2B shows a fitting of an example measurement with the resulting 3-compartment-model equation.

A graphical representation of the three-compartment model for renal function measurement is shown in FIG. 2A.

Kinetic Model

As shown in E. L. Cussler. Diffusion: Mass transfer in fluid systems. Cambridge university press, 1997:

$$\begin{pmatrix} \text{amount of mass} \\ \text{transferred} \end{pmatrix} = k \begin{pmatrix} \text{interfacial} \\ \text{area} \end{pmatrix} \begin{pmatrix} \text{concentration} \\ \text{difference} \end{pmatrix}$$

Since the interfacial area is unknown, it is summarized:

$$R = k \begin{pmatrix} \text{interfacial} \\ \text{area} \end{pmatrix}$$

The mass changes over time in the model of FIG. 2A can be represented as:

$$\frac{dm_H}{dt} = -R_4 \cdot c_H \tag{0.1}$$

$$\frac{dm_P}{dt} = R_4 \cdot c_H - R_1 \cdot c_P - R_2 \cdot c_P + R_3 \cdot c_I \tag{0.2}$$

$$\frac{dm_I}{dt} = R_2 \cdot c_P - R_3 \cdot c_I \tag{0.3}$$

Since the signal is proportional not to the mass $m_I$ but the concentration $c_I$ in the interstitium, the equations 0.1 to 0.3 need to be transformed with eq. 0.5:

$$c = \frac{m}{V} \quad (0.4)$$

$$\frac{dc}{dt} = \frac{1}{V}\frac{dm}{dt} \quad (0.5)$$

With V: Volume $$\frac{dc_H}{dt} = -c_H \cdot \frac{R_4}{V_H} \quad (0.6)$$

$$\frac{dc_P}{dt} = c_H \cdot \frac{R_4}{V_P} - c_P \cdot \frac{R_1 + R_2}{V_P} + c_I \cdot \frac{R_3}{V_P} \quad (0.7)$$

$$\frac{dc_I}{dt} = c_P \frac{R_2}{V_I} - c_I \frac{R_3}{V_I} \quad (0.8)$$

Equation 0.6 can be solved directly:

$$c_H = c_{H,max} \cdot e^{-\frac{R_4}{V_H} \cdot t} \quad (0.9)$$

from eq. 0.8:

$$c_P = \frac{V_I}{R_2} \cdot \frac{dc_I}{dt} + \frac{R_3}{R_2} \cdot c_I \quad (0.10)$$

$$\frac{dc_P}{dt} = \frac{V_I}{R_2} \cdot \frac{d^2 c_I}{dt^2} + \frac{R_3}{R_2} \cdot \frac{dc_I}{dt} \quad (0.11)$$

Using eq. 0.10, 0.9 and 0.11 in eq. 0.7:

$$\frac{V_I}{R_2} \cdot \frac{d^2 c_I}{dt^2} + \frac{R_3}{R_2} \cdot \frac{dc_I}{dt} = \quad (0.12)$$

$$\frac{R_4}{V_P} \cdot c_{H,max} \cdot e^{-\frac{R_4}{V_H} \cdot t} - \frac{R_1 + R_2}{V_P} \cdot \left(\frac{V_I}{R_2} \cdot \frac{dc_I}{dt} + \frac{R_3}{R_2} \cdot c_I\right) + \frac{R_3}{V_P} \cdot c_I$$

$$\frac{d^2 c_I}{dt^2} + \frac{dc_I}{dt} \cdot \left(\frac{R_1 \cdot V_I + R_2 \cdot V_I + R_3 \cdot V_P}{V_P \cdot V_I}\right) + c_I \cdot \left(\frac{R_1 \cdot R_3}{V_P \cdot V_I}\right) =$$

$$\frac{R_2 \cdot R_4}{V_P \cdot V_I} \cdot c_{H,max} \cdot e^{-\frac{R_4}{V_H} \cdot t}$$

Equation 0.12 is an inhomogeneous differential equation of 2nd order with constant coefficients.

Homogeneous Solution $$y_h'' + y_h' \cdot a + y_h \cdot b = 0 \quad (0.13)$$

$$\frac{d^2 y_h}{dt^2} + \frac{dy_h}{dt} \cdot \left(\frac{R_1 \cdot V_I + R_2 \cdot V_I + R_3 \cdot V_P}{V_P \cdot V_I}\right) + y_h \cdot \left(\frac{R_1 \cdot R_3}{V_P \cdot V_I}\right) = 0$$

The solution of 0.13 is:

$$y_h = C_1 \cdot e^{\lambda_1 \cdot t} + C_2 \cdot e^{\lambda_2 \cdot t} \quad (0.14)$$

with $$\lambda_{1,2} = -\frac{a}{2} \pm \sqrt{\frac{a^2}{4} - b}$$

$$\lambda_{1,2} = -\frac{R_1 \cdot V_I \cdot R_2 \cdot V_I + R_3 \cdot V_P}{2 \cdot V_P \cdot V_I} \pm$$

$$\sqrt{\frac{(R_1 \cdot V_I + R_2 \cdot V_I + R_3 \cdot V_P)^2}{4 \cdot V_P^2 \cdot V_I^2} - \frac{R_1 \cdot R_3}{V_P \cdot V_I}}$$

Inhomogeneous Solution $$g(x) = \frac{R_2 \cdot R_4}{V_P \cdot V_I} \cdot c_{H,max} \cdot e^{-\frac{R_4}{V_H} \cdot t} \quad (0.15)$$

$$y_p = C_3 \cdot e^{-\frac{R_4}{V_H} \cdot t} \quad (0.16)$$

$$y_p' = -\frac{R_4}{V_H} \cdot C_3 \cdot e^{-\frac{R_4}{V_H} \cdot t} \quad (0.17)$$

$$y_p'' = \frac{R_4^2}{V_H^2} \cdot C_3 \cdot e^{-\frac{R_4}{V_H} \cdot t} \quad (0.18)$$

$$y_p'' + a \cdot y_p' + b \cdot y_p = g(x)$$

$$\frac{R_4^2}{V_H^2} \cdot C_3 \cdot e^{-\frac{R_4}{V_H} \cdot t} - \frac{R_1 \cdot V_I + R_2 \cdot V_I + R_3 \cdot V_P}{V_P \cdot V_I} \cdot \frac{R_4}{V_H} \cdot C_3 \cdot e^{-\frac{R_4}{V_H} \cdot t} + \quad (0.19)$$

$$\frac{R_1 \cdot R_3}{V_P \cdot V_I} \cdot C_3 \cdot e^{-\frac{R_4}{V_H} \cdot t} = \frac{R_2 \cdot R_4}{V_P \cdot V_I} \cdot c_{H,max} \cdot e^{-\frac{R_4}{V_H} \cdot t}$$

$$C_3 = -\frac{R_2 \cdot R_4 \cdot c_{H,max}}{R_1 \cdot R_4 \cdot \frac{V_I}{V_H} + R_2 \cdot R_4 \cdot \frac{V_I}{V_H} + R_3 \cdot R_4 \cdot \frac{V_P}{V_H} - R_4^2 \cdot \frac{V_P \cdot V_I}{V_H^2} - R_1 \cdot R_3} \quad (0.20)$$

General Solution—Linear Combination of the Homogenous and Inhomogeneous Solution $$c_I(t) = y_h + y_p \quad (0.21)$$

$$c_I(t) = C_1 \cdot e^{\lambda_1 \cdot t} + C_2 \cdot e^{\lambda_2 \cdot t} + C_3 \cdot e^{\lambda_3 \cdot t} \quad (0.22)$$

with $$c_I(0) = 0 \quad (0.23)$$

can be simplified:

$$0 = C_1 + C_2 + C_3$$

$$A = -C_2$$

$$B = -C_3$$

$$C_1 = A + B$$

Interstitial Concentration $C_I$ $$c_I = (A + B) \cdot e^{\lambda_1 \cdot t} - A \cdot e^{\lambda_2 \cdot t} - B \cdot e^{\lambda_3 \cdot t} \quad (0.24)$$

with

-continued $$\lambda_{1,2} = -\frac{R_1 \cdot V_I + R_2 \cdot V_I + R_3 \cdot V_P}{2 \cdot V_P \cdot V_I} \pm \sqrt{\frac{(R_1 \cdot V_I + R_2 \cdot V_I + R_3 \cdot V_P)^2}{4 \cdot V_P^2 \cdot V_I^2} - \frac{R_1 \cdot R_3}{V_P \cdot V_I}} \quad (0.25)$$

$$\lambda_3 = -\frac{R_4}{V_H} \quad (0.26)$$

$$B = \frac{R_2 \cdot R_4 \cdot c_{H,max}}{R_1 \cdot R_4 \cdot \frac{V_I}{V_H} + R_2 \cdot R_4 \cdot \frac{V_I}{V_H} + R_3 \cdot R_4 \cdot \frac{V_P}{V_H} - R_4^2 \cdot \frac{V_P \cdot V_I}{V_H^2} - R_1 \cdot R_3} \quad (0.27)$$

With 0.8:

$$\frac{dc_I}{dt} = c_P \frac{R_2}{V_I} - c_I \cdot \frac{R_3}{V_I}$$

$$c_P(0) = 0$$

$$c_I(0) = 0$$

$$\frac{dc_I(0)}{dt} = 0$$

For the first derivative of eq. 0.24:

$$\frac{dc_I(t)}{dt} = \lambda_1 \cdot (A + B) \cdot e^{\lambda_1 \cdot t} - \lambda_2 \cdot A \cdot e^{\lambda_2 \cdot t} - \lambda_3 \cdot B \cdot e^{\lambda_3 \cdot t} \quad (0.28)$$

$$\frac{dc_I(0)}{dt} = 0 = \lambda_1 \cdot (A + B) - \lambda_2 \cdot A - \lambda_3 \cdot B$$

$$A = B \cdot \frac{\lambda_1 - \lambda_3}{\lambda_2 - \lambda_1}$$

Plasma Concentration $c_p$
With eq.0.8 $c_p$ is $$c_P = \frac{V_I}{R_2} \cdot \frac{dc_I}{dt} + \frac{R_3}{R_2} \cdot c_I \quad (0.29)$$

$$c_P = (A + B) \cdot e^{\lambda_1 \cdot t} \cdot \frac{V_I \cdot \lambda_1 + R_3}{R_2} - A \cdot e^{\lambda_2 \cdot t} \cdot \frac{V_I \cdot \lambda_2 + R_3}{R_2} - B \cdot e^{\lambda_3 \cdot t} \cdot \frac{V_I \cdot \lambda_3 + R_3}{R_2}$$

Another form for eq. 0.29 is:

$$c_P = B^* \cdot [(\lambda_2 - \lambda_3) \cdot (V_I \cdot \lambda_1 + R_3) \cdot e^{\lambda_1 \cdot t} - (\lambda_1 - \lambda_3) \cdot (V_I \cdot \lambda_2 + R_3) \cdot e^{\lambda_2 \cdot t} - (\lambda_2 - \lambda_1) \cdot (V_I \cdot \lambda_3 + R_3) \cdot e^{\lambda_3 \cdot t}] \quad (0.30)$$

with $$B^* = \frac{B}{R_2 \cdot (\lambda_2 - \lambda_1)} \quad (0.31)$$

Example 3

Four-Compartment Model

Figure 3A:
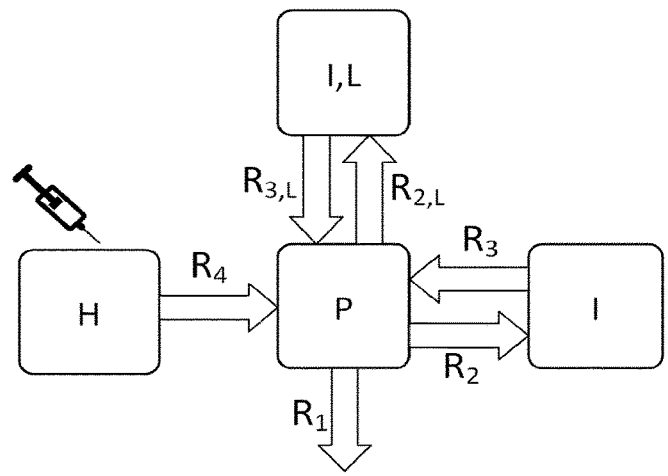
FIG. 3A shows a graphical representation of a 4-compartment model for renal function measurement.
Figure 3B:
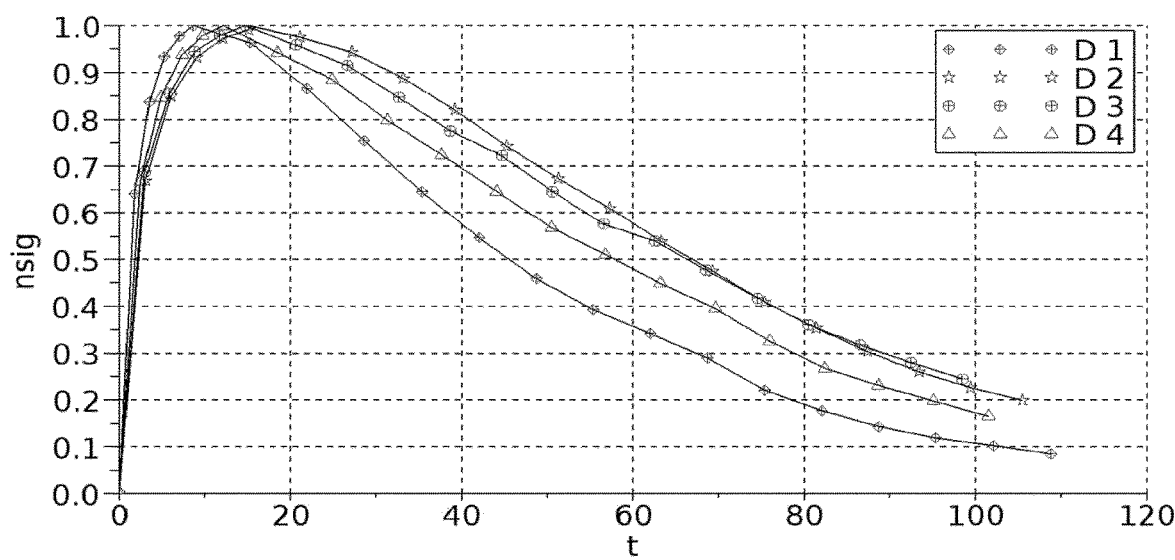
FIG. 3B shows an example measurement with four simultaneously recorded concentration-time curves.
Figure 3C:
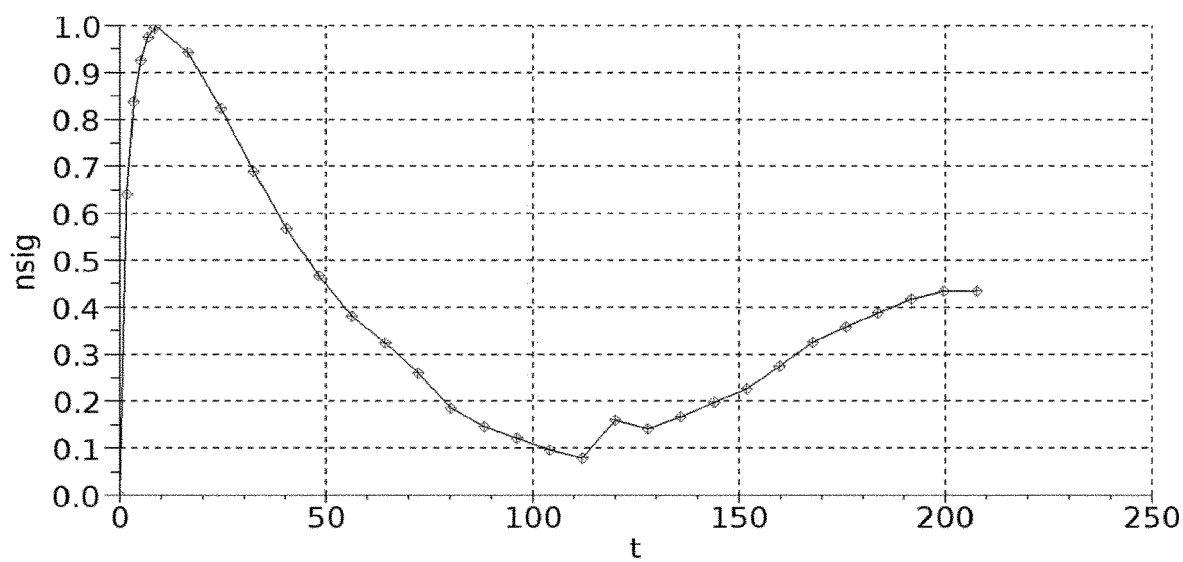
FIG. 3C shows a measurement of bolus injection followed by constant infusion until steady state is reached.

A graphical representation of the four-compartment model for renal function measurement is shown in FIG. 3A.

Local Interstitium $c_{I,L}$

Due to local variations in the skin qualities there are differences in simultaneously measured excretion curves. To address this problem, a compartment 'Local Interstitium' is introduced. Two simultaneous measurements are used to eliminate the local differences.

The differential equation for $c_{I,L}$ is:

$$\frac{dm_{I,L}}{dt} = -c_{I,L} \cdot R_{3,L} + c_P \cdot R_{2,L} \quad (0.32)$$

$$\frac{dc_{I,L}}{dt} = -c_{I,L} \cdot \frac{R_{3,L}}{V_{I,L}} + c_P \cdot \frac{R_{2,L}}{V_{I,L}} \quad (0.33)$$

Since the local interstitium is very small compared to the rest of the system, the assumption that the plasma marker concentration is not altered by the tiny mass flow $dm_{I,L}/dt$ is made. So for $C_P$ equation 0.30 can be used:

$$\frac{dc_{I,L}}{dt} = -c_{I,L} \cdot \frac{R_{3,L}}{V_{I,L}} + B^{**} \cdot [(\lambda_2 - \lambda_3) \cdot (V_I \cdot \lambda_1 + R_3) \cdot e^{\lambda_1 \cdot t} - (\lambda_1 - \lambda_3) \cdot (V_I \cdot \lambda_2 + R_3) \cdot e^{\lambda_2 \cdot t} - (\lambda_2 - \lambda_1) \cdot (V_I \cdot \lambda_3 + R_3) \cdot e^{\lambda_3 \cdot t}] \quad (0.34)$$

with $$B^{**} = B^* \cdot \frac{R_{2,L}}{V_{I,L}} \quad (0.35)$$

Homogenous Solution $$\frac{dc_{I,L}}{dt} + c_{I,L} \cdot \frac{R_{3,L}}{V_{I,L}} = 0 \quad (0.36)$$

$$c_{I,L} = K(t) \cdot e^{-\frac{R_{3,L}}{V_{I,L}} \cdot t} \quad (0.37)$$

Inhomogeneous Solution $$g(t) = B^{**} \cdot [(\lambda_2 - \lambda_3) \cdot (V_I \cdot \lambda_1 + R_3) \cdot e^{\lambda_1 \cdot t} - (\lambda_1 - \lambda_3) \cdot (V_I \cdot \lambda_2 + R_3) \cdot e^{\lambda_2 \cdot t} - (\lambda_2 - \lambda_1) \cdot (V_I \cdot \lambda_3 + R_3) \cdot e^{\lambda_3 \cdot t}] \quad (0.38)$$

$$K(t) = \int g(t) \cdot e^{\frac{R_{3,L}}{V_{I,L}} \cdot t} \cdot dt + G \quad (0.39)$$

$$K(t) = B^{**} \cdot \left[ \frac{(\lambda_2 - \lambda_3) \cdot (V_I \cdot \lambda_1 + R_3)}{\lambda_1 + \frac{R_{3,L}}{V_{I,L}}} \cdot e^{\left(\lambda_1 + \frac{R_{3,L}}{V_{I,L}}\right) \cdot t} - \frac{(\lambda_1 - \lambda_3) \cdot (V_I \cdot \lambda_2 + R_3)}{\lambda_2 + \frac{R_{3,L}}{V_{I,L}}} \cdot e^{\left(\lambda_2 + \frac{R_{3,L}}{V_{I,L}}\right) \cdot t} - \frac{(\lambda_2 - \lambda_1) \cdot (V_I \cdot \lambda_3 + R_3)}{\lambda_3 + \frac{R_{3,L}}{V_{I,L}}} \cdot e^{\left(\lambda_3 + \frac{R_{3,L}}{V_{I,L}}\right) \cdot t} \right] + G \quad (0.40)$$

General Solution $$c_{I,L}(t) = \qquad (0.41)$$

$$B^{**} \cdot \left[ \frac{(\lambda_2 - \lambda_3) \cdot (V_I \cdot \lambda_1 \cdot R_3)}{\lambda_1 + \frac{R_{3,L}}{V_{I,L}}} \cdot e^{\lambda_1 \cdot t} - \frac{(\lambda_1 - \lambda_3) \cdot (V_I \cdot \lambda_2 + R_3)}{\lambda_2 + \frac{R_{3,L}}{V_{I,L}}} \cdot \right.$$

$$\left. e^{\lambda_2 \cdot t} - \frac{(\lambda_2 - \lambda_1) \cdot (V_I \cdot \lambda_3 + R_3)}{\lambda_3 + \frac{R_{3,L}}{V_{I,L}}} \cdot e^{\lambda_3 \cdot t} \right] + G \cdot e^{-\frac{R_{3,L}}{V_{I,L}} \cdot t}$$

With $c_{I,L}(0) = 0$ $$G = -B^{**} \cdot \left[ \frac{(\lambda_2 - \lambda_3) \cdot (V_I \cdot \lambda_1 \cdot R_3)}{\lambda_1 + \frac{R_{3,L}}{V_{I,L}}} - \right. \qquad (0.42)$$

$$\left. \frac{(\lambda_1 - \lambda_3) \cdot (V_I \cdot \lambda_2 + R_3)}{\lambda_2 + \frac{R_{3,L}}{V_{I,L}}} - \frac{(\lambda_2 - \lambda_1) \cdot (V_I \cdot \lambda_3 + R_3)}{\lambda_3 + \frac{R_{3,L}}{V_{I,L}}} \right]$$

leading to:

$$c_{I,L}(t) = B^{**} \cdot \left[ \frac{(\lambda_2 - \lambda_3) \cdot (V_I \cdot \lambda_1 \cdot R_3)}{\lambda_1 + \frac{R_{3,L}}{V_{I,L}}} \cdot \left( e^{\lambda_1 \cdot t} - e^{-\frac{R_{3,L}}{V_{I,L}} \cdot t} \right) - \right. \qquad (0.43)$$

$$\frac{(\lambda_1 - \lambda_3) \cdot (V_I \cdot \lambda_2 + R_3)}{\lambda_2 + \frac{R_{3,L}}{V_{I,L}}} \cdot \left( e^{\lambda_2 \cdot t} - e^{-\frac{R_{3,L}}{V_{I,L}} \cdot t} \right) -$$

$$\left. \frac{(\lambda_2 - \lambda_1) \cdot (V_I \cdot \lambda_3 + R_3)}{\lambda_3 + \frac{R_{3,L}}{V_{I,L}}} \cdot \left( e^{\lambda_3 \cdot t} - e^{-\frac{R_{3,L}}{V_{I,L}} \cdot t} \right) \right]$$

Measured Signal $c_M$

The measured signal is a combined signal from the local interstitium $c_{I,L}$ and a very diminished signal from the plasma (vessels near the sensor). The plasma signal is strongly diminished through absorption of the green wavelength in the hemoglobin.

$$c_M = \alpha \cdot (c_{I,L} + \chi \cdot c_P) \qquad (0.44)$$

$\alpha \in \mathbb{R}$ amplification factor due to electronic components
$\chi \in \mathbb{R}$ diminishing factor $0 \leq \chi \leq 1$ $fac_1 = \chi \cdot \alpha$
$fac_2 = \alpha$ for the measured curve $c_M$:

$$c_M(t) = fac_1 \cdot c_P(t) + fac_2 \cdot c_{I,L}(t) \qquad (0.45)$$

with $$D = B^* \cdot fac_1 \qquad (0.46)$$

$$E = B^{**} \cdot fac_2 \qquad (0.47)$$

$$c_M(t) = \qquad (0.48)$$
$$D \cdot [(\lambda_2 - \lambda_3) \cdot (V_I \cdot \lambda_1 + R_3) \cdot e^{\lambda_1 \cdot t} - (\lambda_1 - \lambda_3) \cdot (V_I \cdot \lambda_2 + R_3) \cdot e^{\lambda_2 \cdot t} - (\lambda_2 - \lambda_1) \cdot (V_I \cdot \lambda_3 + R_3) \cdot e^{\lambda_3 \cdot t}] +$$

$$E \cdot \left[ \frac{(\lambda_2 - \lambda_3) \cdot (V_I \cdot \lambda_1 + R_3)}{\lambda_1 + \frac{R_{3,L}}{V_{I,L}}} \cdot \left( e^{\lambda_1 \cdot t} - e^{-\frac{R_{3,L}}{V_{I,L}} \cdot t} \right) - \right.$$

$$\frac{(\lambda_1 - \lambda_3) \cdot (V_I \cdot \lambda_2 + R_3)}{\lambda_2 + \frac{R_{3,L}}{V_{I,L}}} \cdot \left( e^{\lambda_2 \cdot t} - e^{-\frac{R_{3,L}}{V_{I,L}} \cdot t} \right) -$$

$$\left. \frac{(\lambda_2 - \lambda_1) \cdot (V_I \cdot \lambda_3 + R_3)}{\lambda_3 + \frac{R_{3,L}}{V_{I,L}}} \cdot \left( e^{\lambda_3 \cdot t} - e^{-\frac{R_{3,L}}{V_{I,L}} \cdot t} \right) \right]$$

Simplification: $R_2 = R_3$

For the diffusion between plasma and interstitium the diffusion constants forth and backwards should be equal:

$$R_2 = R_3 = R_{23} \qquad (0.49)$$

thus, equation 0.25 simplifies to:

$$\lambda_{1,2} = -\frac{R_1 \cdot V_I + R_{23} \cdot (V_I + V_P)}{2 \cdot V_P \cdot V_I} \pm \qquad (0.50)$$

$$\sqrt{\frac{(R_1 \cdot V_I + R_{23} \cdot (V_I + V_P))^2}{4 \cdot V_P^2 \cdot V_I^2} - \frac{R_1 \cdot R_{23}}{V_P \cdot V_I}}$$

$$\lambda_{1,2} = \qquad (0.51)$$
$$-\frac{1}{2}\left(\frac{R_1}{V_P} + \frac{R_{23}}{V_P} + \frac{R_{23}}{V_I}\right) \pm \sqrt{\frac{1}{4}\left(\frac{R_1}{V_P} + \frac{R_{23}}{V_P} + \frac{R_{23}}{V_I}\right)^2 - \frac{R_1}{V_P} \cdot \frac{R_{23}}{V_I}}$$

$$\lambda_1 \cdot \lambda_2 = \frac{R_1}{V_P} \cdot \frac{R_{23}}{V_I} \qquad (0.52)$$

$$\lambda_1 + \lambda_2 = -\left(\frac{R_1}{V_P} + \frac{R_{23}}{V_P} + \frac{R_{23}}{V_I}\right) \qquad (0.53)$$

Equation 0.52 can be transformed to:

$$R_{23} = \frac{V_I \cdot V_P \cdot \lambda_1 \cdot \lambda_2}{R_1} \qquad (0.54)$$

Fit Function

Equation 0.54 can be used to replace $R_{23}$ in equation 0.48:

$$c_M(t) =$$
$$D \cdot \left[ (\lambda_2 - \lambda_3) \cdot \lambda_1 \cdot V_I \cdot \left(1 + \frac{V_P}{R_1} \cdot \lambda_2\right) \cdot e^{\lambda_1 \cdot t} - (\lambda_1 - \lambda_3) \cdot \lambda_2 \cdot V_I \cdot \left(1 + \frac{V_P}{R_1} \cdot \lambda_1\right) \cdot \right.$$

$$\left. e^{\lambda_2 \cdot t} - (\lambda_2 - \lambda_1) \cdot V_I \cdot \left(\lambda_3 + \frac{V_P}{R_1} \cdot \lambda_1 \cdot \lambda_2\right) \cdot e^{\lambda_3 \cdot t} \right] +$$

$$E \cdot \left[ \frac{(\lambda_2 - \lambda_3) \cdot \lambda_1 \cdot V_I \cdot \left(1 + \frac{V_P}{R_1} \cdot \lambda_2\right)}{\lambda_1 + \frac{R_{3,L}}{V_{I,L}}} \cdot \left( e^{\lambda_1 \cdot t} - e^{-\frac{R_{3,L}}{V_{I,L}} \cdot t} \right) - \right.$$

-continued $$\frac{(\lambda_1 - \lambda_3) \cdot \lambda_2 \cdot V_I \cdot \left(1 + \frac{V_P}{R_1} \cdot \lambda_1\right)}{\lambda_2 + \frac{R_{3,L}}{V_{I,L}}} \cdot \left(e^{\lambda_2 \cdot t} - e^{-\frac{R_{3,L}}{V_{I,L}} \cdot t}\right) -$$

$$\frac{(\lambda_2 - \lambda_1) \cdot V_I \cdot \left(\lambda_3 + \frac{V_P}{R_1} \cdot \lambda_1 \cdot \lambda_2\right)}{\lambda_3 + \frac{R_{3,L}}{V_{I,L}}} \cdot \left(e^{\lambda_3 \cdot t} - e^{-\frac{R_{3,L}}{V_{I,L}} \cdot t}\right)\Bigg]$$

which can be simplified with:

$$D^* = D \cdot V_I \tag{0.55}$$

$$E^* = E \cdot V_I \tag{0.56}$$

to $$c_M(t) = D^* \cdot \left[(\lambda_2 - \lambda_3) \cdot \left(\lambda_1 + \frac{V_P}{R_1} \cdot \lambda_1 \cdot \lambda_2\right) \cdot e^{\lambda_1 \cdot t} - \right. \tag{0.57}$$

$$(\lambda_1 - \lambda_3) \cdot \left(\lambda_2 + \frac{V_P}{R_1} \cdot \lambda_1 \cdot \lambda_2\right) \cdot e^{\lambda_2 \cdot t} -$$

$$(\lambda_2 - \lambda_1) \cdot \left(\lambda_3 + \frac{V_P}{R_1} \cdot \lambda_1 \cdot \lambda_2\right) \cdot e^{\lambda_3 \cdot t}\Bigg] +$$

$$E^* \cdot \Bigg[\frac{(\lambda_2 - \lambda_3) \cdot \left(\lambda_1 + \frac{V_P}{R_1} \cdot \lambda_1 \cdot \lambda_2\right)}{\lambda_1 + \frac{R_{3,L}}{V_{I,L}}} \cdot \left(e^{\lambda_1 \cdot t} - e^{-\frac{R_{3,L}}{V_{I,L}} \cdot t}\right) -$$

$$\frac{(\lambda_1 - \lambda_3) \cdot \left(\lambda_2 + \frac{V_P}{R_1} \cdot \lambda_1 \cdot \lambda_2\right)}{\lambda_2 + \frac{R_{3,L}}{V_{I,L}}} \cdot \left(e^{\lambda_2 \cdot t} - e^{-\frac{R_{3,L}}{V_{I,L}} \cdot t}\right) -$$

$$\frac{(\lambda_2 - \lambda_1) \cdot \left(\lambda_3 + \frac{V_P}{R_1} \cdot \lambda_1 \cdot \lambda_2\right)}{\lambda_3 + \frac{R_{3,L}}{V_{I,L}}} \cdot \left(e^{\lambda_3 \cdot t} - e^{-\frac{R_{3,L}}{V_{I,L}} \cdot t}\right)\Bigg]$$

Function 0.57 is used to fit data of two simultaneous measurements with parameters being either global (same value for both curves) or local—see Table 1:

TABLE 1

Global and local parameters of fit function 0.57

| Parameter | global | local | Range |
|---|---|---|---|
| $\lambda_{1,3}$ | ✓ | | <0 |
| $\frac{V_P}{R_1}$ | ✓ | | >0 |
| $\frac{R_{3,L}}{V_{I,L}}$ | | ✓ | >0 |
| $D^*$ | | ✓ | >0 |
| $E^*$ | | ✓ | >0 |

In function 0.57 only quotients of R and V can be directly determined. When the quotient of $V_P/R_1$ is determined, the plasma volume $V_P$ is needed to get to R1. Vp becomes an input parameter and can be determined by an independent experiment or from literature values, e.g. Probst et al., (2006), Journal of the American Association for Laboratory Animal Science: J A ALAS, 45(2): 49.

$$\frac{dm_P}{dt} = -R_1 \cdot c_P + R_{23} \cdot (c_I - c_P) + \dot{m}_{in} \tag{0.58}$$

$$\frac{dm_I}{dt} = R_{23} \cdot (c_P - c_I) \tag{0.59}$$

can be expressed as $$\frac{dc_P}{dt} = -c_P \cdot \frac{R_1}{V_P} + (c_I - c_P) \cdot \frac{R_{23}}{V_P} + \frac{\dot{m}_{in}}{V_P} \tag{0.60}$$

$$\frac{dc_I}{dt} = \frac{R_{23}}{V_I} \cdot (c_P - c_I) \tag{0.61}$$

yields the following differential equation:

$$\frac{d^2 c_I}{dt^2} + \frac{dc_I}{dt} \cdot \left(\frac{R_{23}}{V_I} + \frac{R_1}{V_P} + \frac{R_{23}}{V_P}\right) + c_I \cdot \frac{R_1 \cdot R_{23}}{V_I \cdot V_P} = \dot{m}_{in} \cdot \frac{R_{23}}{V_I \cdot V_P} \tag{0.62}$$

For $c_I$ and $c_p$:

$$c_I(t) = A \cdot e^{\lambda_1 \cdot t} + B \cdot e^{\lambda_2 \cdot t} + \frac{\dot{m}_{in}}{R_1} \tag{0.63}$$

$$c_P(t) = A \cdot e^{\lambda_1 \cdot t} \cdot \left(1 + \frac{V_I \cdot \lambda_1}{R_{23}}\right) + B \cdot e^{\lambda_2 \cdot t} \cdot \left(1 + \frac{V_I \cdot \lambda_2}{R_{23}}\right) + \frac{\dot{m}_{in}}{R_1} \tag{0.64}$$

For the steady state:

$$c_{P,s} = \lim_{t \to \infty} c_P = \frac{\dot{m}_{in}}{R_1} \tag{0.65}$$

Relation between $R_1$ and GFR $$GFR = \frac{V_{glom\text{-}Filtrat}}{t} \tag{0.66}$$

$$\dot{m}_{Marker, glom\text{-}Filtrat} = \dot{m}_{Marker, Harn} \tag{0.67}$$

$$\dot{m}_{Marker, Harn} = \dot{m}_{Marker, in} \tag{0.68}$$

$$c_{Marker, glom\text{-}Filtrat} = c_{Marker, Plasma} \tag{0.69}$$

$$\frac{c_{Marker, Plasma} \cdot V_{glom\text{-}Filtrat}}{t} = \frac{c_{Marker, Harn} \cdot V_{Harn}}{t} \tag{0.70}$$

$$GFR = \frac{c_{Marker, Harn} \cdot V_{Harn}}{t \cdot c_{Marker, Plasma}} \tag{0.71}$$

$$GFR = \frac{\dot{m}_{Marker, in}}{c_{Marker, Plasma}} \tag{0.72}$$

-continued $$R_1 = \frac{\dot{m}_{Marker,in}}{c_{Marker,Plasma}} \quad (0.73)$$

$$R_1 = GFR \quad (0.74)$$

Thus, $R_1$ equals the GFR.

Example 4

Experimental Validation

1 Introduction 1.1 Purpose

The pharmacokinetic model was validated by the following experiment. The distribution and excretion kinetic of the marker is determined by fluorescence measurement on the skin after an i.v. bolus injection in laboratory animals using four NIC-Kidney devices. After 120 min, when most of the marker is excreted, a constant infusion with the same marker is started until a steady state is reached. In this state blood samples are taken to determine the plasma concentration of the marker. The constant infusion experiment is accounted as gold standard method for GFR assessment and allows validation of the results of GFR assessment of the bolus experiment combined with the novel pharmacokinetic model (Schock-Kusch et al. (2012) Kidney Int. 82(3): 314-20).

1.2 Equipment

One NIC-Kidney device with radio frequency unit (RF-Device) for real-time data observation (Mannheim Pharma& Diagnostics GmbH, Mannheim Germany)
Three NIC-Kidney devices with internal memory (Mannheim Pharma & Diagnostics GmbH, Mannheim Germany)

Infusion Pump

Equipment for blood sampling and fluorescence measurement in plasma as described elsewhere (Kidney International 2011 June; 79(1 1): 1254-8).

1.3 Animals

Male Sprague-Dawley(SD) rats with a body weight of 300-350 g. The measurements are conducted on awake animals. Number of animals n=6.

1.4 Drugs

Injection solution bolus: FITC-Sinistrin 40 mg/ml(Mannheim Pharma& Diagnostics GmbH, Mannheim Germany)
Injection solution constant infusion: FITC-Sinistrin 15 mg/ml
Bolus dose: 5 mg/100 g b.w.
Flow rate of pump during constant infusion: 0.01 ml/min
Isofluran(Baxter Deutschland GmbH)

2 Protocol 2.1 Treatment

The animals undergo the standard preparations of catheterization and shaving as described by Schock-Kusch et al. (Kidney International 2011 June; 79(11): 1254-8). To attach the devices the animals are anaesthetized with Isofluran.

After the devices are attached they should be switched on 10 min prior to injection. One blood sample has to be taken before the injection.

2.2 Bolus Part

After the FITC-Sinistrin injection at t=0 the bolus experiment lasts for t=120 min (Kidney International 2011 June; 79(11): 1254-8). During this period all 4 devices record data.

2.3 Constant Infusion Part

At t>120 min the infusion pump is switched on and the fluorescence level is monitored via the RF-device. After reaching a plateau 2 blood samples are taken in a 10 min interval. The FITC-Sinistrin concentrations in the plasma of these samples are determined by fluorescence measurement as described elsewhere (Nephrol Dial Transplant. 2009 October; 24(10): 2997-3001).

2.4 Data Processing

From the gained data the GFR is assessed according to the constant infusion technique (Kidney Int. 2012 August; 82(3): 314-20), and from combinations of pairs of the four excretion kinetics assessed during the bolus experiment (6 pairs total) using the novel pharmacological model.

2.5 Sample Curve

See FIG. 3

2.6 Results

Fitting pairs of device combinations with eq. (0.57)

|  | Device Combination | | | | | |
|---|---|---|---|---|---|---|
|  | 1 & 2 | 1 & 4 | 1 & 3 | 2 & 4 | 2 & 3 | 4 & 3 |
| GFR/VP [l/min] | 0.12 | 0.14 | 0.11 | 0.10 | 0.12 | 0.13 |

The animal (healthy SD rat) had a body weight of m=309 g. With a plasma volume per body weight rate of 0.0412 ml/g (R. J. Probst, J. M. Lim, D. N. Bird, G. L. Pole, A. K. Sato, and J. R. Claybaugh. Gender differences in the blood volume of conscious Sprague-Dawley rats. Journal of the American Association for Laboratory Animal Science: JAA-LAS, 45(2):49, 2006) the plasma volume is VP=12.7 ml.

|  | Device Combination | | | | | |
|---|---|---|---|---|---|---|
|  | 1 & 2 | 1 & 4 | 1 & 3 | 2 & 4 | 2 & 3 | 4 & 3 |
| GFR [ml/min] | 1.50 | 1.78 | 1.46 | 1.30 | 1.50 | 1.62 |

The blood samples taken during the following constant infusion experiment showed an average marker concentration of 0.093 mg/ml. With a mass flow marker into the animal of 0.15 mg/min the GFR results in GFR=1.61 ml/min (see equation (0.65)).

The invention claimed is:

1. A method for determining an organ function in a subject in need thereof, the method comprising:
    administering a fluorescent indicator compound to the bloodstream of the subject;
    measuring transcutaneously a first concentration-time curve in a first body fluid at a first position on the subject, wherein said first concentration time curve comprises (i) at least one data point collected prior to administering the fluorescent indicator compound to the bloodstream of the subject as a first background time point, and (ii) at least five data points collected after administering the fluorescent indicator compound to the subject;
    measuring transcutaneously a second concentration-time curve in a second body fluid at a second position on the subject, wherein said second concentration time curve comprises (i) at least one data point collected prior to administering the fluorescent indicator compound to the bloodstream of the subject as a second background time point, and (ii) at least five data points collected after administering the fluorescent indicator compound to the subject;
    fitting the first and the second concentration-time curve into a kinetic model representing two or three diffusion compartments, wherein the diffusion compartments are selected from the group consisting of plasma, interstitial fluid, local interstitium at the position of the measuring, and distribution; and
    determining the organ function of the subject based on the results of fitting the first concentration-time curve and the second concentration-time curve into the kinetic model;
    wherein the first position and the second position on the body of the subject are different, the first body fluid and the second body fluid of the subject may be the same or different, and measuring fluorescence of the indicator compound at the first position and the second position is performed simultaneously.

2. The method according to claim 1, wherein administering is performed orally, intraarterially, intravenously, or as a bolus injection.

3. The method according to claim 1, wherein the fluorescent indicator compound is only eliminated from the bloodstream of the patient by glomerular filtration.

4. The method according to claim 1, wherein the kinetic model represents two diffusion compartments.

5. The method according to claim 1, wherein the kinetic model represents three diffusion compartments.

6. The method according to claim 1, wherein the method further comprises determining the blood volume of the patient.

7. The method according to claim 1, wherein the organ function is the glomerular filtration rate (GFR).

8. The method of claim 1, wherein at least at least one of the data points for the first concentration-time curve and at least one of the data points for the second concentration-time curve is collected within two hours or less after administering the fluorescent indicator compound to the subject.

9. A device configured to implement the method of claim 1, said device comprising:
    a first sensor for transcutaneously measuring fluorescence of the indicator at the first position;
    a second sensor for transcutaneously measuring fluorescence of the indicator at the second position; and
    a data processing unit for fitting the values obtained by the sensors into the kinetic model;
    wherein said first sensor and said second sensor are operatively linked in that the data processing unit of the device is configured to bring together the results of the measurements performed by said sensors and fits the data into the kinetic model.

10. The device of claim 9, further comprising a data storage unit comprising at least reference values of total plasma volume correlated to body mass.

11. A kit comprising the device of claim 9 and the fluorescent indicator compound.

12. The kit of claim 11, wherein the indicator compound comprises a fluorescent low-molecular weight compound covalently bound to a hydrophilic compound, wherein the hydrophilic part is selected from the list consisting of oligo- and polysaccharides, oligo- and polyalcohols, and oligo- and polyethers.

13. A non-transitory computer readable medium comprising an executable computer program configured to perform the method according to claim 1, while the program is being executed on a computer.

14. A computer or computer network comprising at least one processor, wherein the computer or computer network is configured to perform the method according to claim 1.

* * * * *